United States Patent [19]

Holtz et al.

[11] 4,088,823

[45] May 9, 1978

[54] PROMOTED LIQUID PHASE OXIDATION OF ALKYL AROMATIC COMPOUNDS

[75] Inventors: Hans D. Holtz; Lloyd E. Gardner, both of Bartlesville, Okla.

[73] Assignee: Phillips Petroleum Company, Bartlesville, Okla.

[21] Appl. No.: 620,465

[22] Filed: Oct. 7, 1975

[51] Int. Cl.$^2$ .................... C07C 29/00; C07C 51/33; C07C 67/05

[52] U.S. Cl. ................ 560/236; 260/524 R; 260/524 N; 260/592; 260/599; 260/650 R; 560/241; 568/808; 568/815; 568/715; 568/812

[58] Field of Search ........... 260/491, 488 CD, 618 R, 260/618 CD, 618 F, 524 R, 524 N, 599, 592

[56] References Cited

U.S. PATENT DOCUMENTS

| | | | |
|---|---|---|---|
| 3,047,616 | 7/1962 | Blair et al. | 260/488 CD |
| 3,649,674 | 3/1972 | Koehl | 260/488 CD |
| 3,780,094 | 12/1973 | Herz | 260/488 CD |

*Primary Examiner*—Vivian Garner

[57] ABSTRACT

A process is provided for oxygenating alkyl-substituted aromatic compounds. In the process alkyl-substituted aromatic compounds are contacted with molecular oxygen in the presence of a suitable monocarboxylic acid, a soluble copper, cobalt, or iron compound, and an inorganic bromine compound. Optionally present are inorganic nitrates, acetic anhydride, or water. In an embodiment of the invention the process is carried out in two distinct steps with contact of the alkyl-substituted aromatic compounds and oxygen in the presence of the essential components produce an ester comprising both an aromatic alcohol and the carboxylic acid with subsequent hydrolyzing of this ester to produce an aromatic alcohol with regeneration of the carboxylic acid.

11 Claims, 1 Drawing Figure

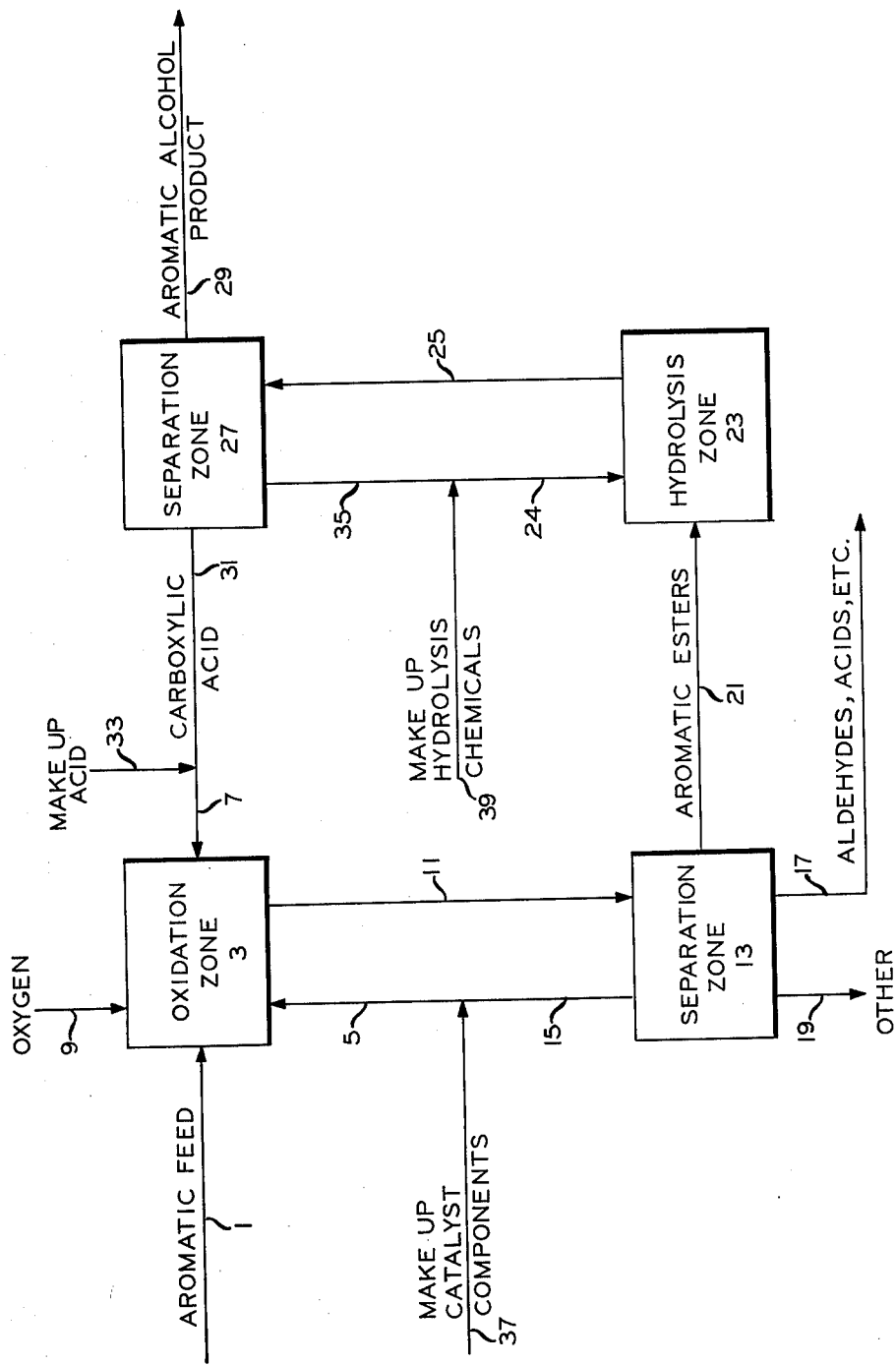

PROMOTED LIQUID PHASE OXIDATION OF ALKYL AROMATIC COMPOUNDS

BACKGROUND OF THE INVENTION

This invention relates to the oxidation of hydrocarbons. In one of its aspects this invention relates to the oxidation of alkyl-substituted hydrocarbons. In still another of its aspects this invention relates to liquid phase processes for the oxidative conversion of alkyl-substituted aromatic compounds to oxygen-containing products. In yet another aspect it relates to the production of oxidation products such as aromatic alcohols, aldehydes, and esters.

It has heretofore been known that relatively plentiful hydrocarbons can be converted to other less plentiful and therefore more valuable organic compounds by processes such as oxidation. For example, alkyl-substituted hydrocarbons such as toluene have been converted to oxygenated products such as benzaldehyde in vapor phase oxidation processes using various catalyst system.

The present invention provides a liquid phase process for the oxidative conversion of alkyl-substituted aromatic compounds to oxygen-containing products which can be used as an alternative process to those already known. The process is particularly applicable for producing products in an intermediate stage of oxidation such as aromatic alcohols, aldehydes, and esters. The process employs the presence of a monocarboxylic acid, hence the alcohol products are obtained principally in the form of esters of the carboxylic acid. If desired, the esters can be readily hydrolyzed to liberate the alcohols, and the monocarboxylic acid can be recycled.

It is an object of this invention to provide a method for producing oxidation products from the conversion of alkyl-substituted aromatics.

Other objects, aspects and the advantages of this invention will become apparent upon reading the specification and the appended claims.

STATEMENT OF THE INVENTION

According to the process of the present invention, an alkyl-substituted aromatic compound is converted to oxygenated products in a liquid phase operation by contacting the alkyl-substituted aromatic compound with molecular oxygen in the presence of a suitable monocarboxylic acid, a minor amount of a soluble copper, cobalt or iron compound, and a minor amount of a suitable inorganic bromide compound. Optionally, the reaction can be carried out in the additional presence of minor amounts of water or acetic anhydride or a suitable inorganic nitrate compound or a compound convertible to a nitrate under conditions of the reaction.

In one embodiment of the present invention, alkyl-substituted aromatic compounds are converted to the corresponding aromatic alcohols in a multi-step process comprising, as a first step, reacting a suitable aromatic feed compound with molecular oxygen, a monocarboxylic acid, a soluble copper, cobalt or iron compound, and an inorganic bromide compound, optionally in the presence of an inorganic nitrate compound, water or acetic anhydride, to produce an ester of an aromatic alcohol and of the carboxylic acid; and, as a second step, hydrolyzing the ester from step 1 to produce an aromatic alcohol product and to regenerate the monocarboxylic acid for recycle to step 1.

The alkyl-substituted aromatic compounds which can be used as feedstocks for the present invention are those aromatic compounds with oxidizable alkyl substituents. Generally these compounds will correspond to the following generic formulas

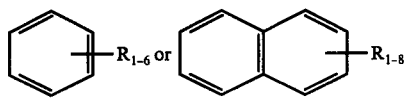

wherein each R is selected from branched or unbranched alkyl groups having from one to about 6 carbon atoms, more usually from 1 to about 4 carbon atoms, or halogen atoms, at least one R being an alkyl group free of quaternary carbon atoms. Usually, such compounds will contain 1-2 alkyl groups and 0-1 halogen atoms.

Some examples of such suitable feedstocks are: toluene, p-tertbutyltoluene, o-xylene, m-xylene, p-xylene, 1,2,4-trimethylbenzene, 1,3,5-trimethylbenzene, 1,2,4,5-tetramethylbenzene, p-chlorotoluene, ethylbenzene, p-isopropyltoluene, isopropylbenzene, n-butylbenzene, p-propyltoluene, m-bromotoluene, α-methylnaphthalene, β-isopropylnaphthalene, n-hexylbenzene, and the like, and mixtures thereof.

The carboxylic acids which are suitable for use in the present invention process are those alkanoic acids having from 1 to about 6 carbon atoms per molecule. Some examples of these are formic acid, acetic acid, propionic acid, butyric acid, 3-methylbutyric acid, pentanoic acid, hexanoic acid, and the like, and mixtures thereof. Acetic acid is particularly effective and convenient.

The soluble copper, cobalt or iron compounds which are used in the catalyst system of the present invention are those which have a significant solubility in the reaction mixture under conditions of the oxidative conversion. As a practical matter, the compounds which are most useful are compounds such as cupric bromide, cuprous bromide, cupric acetate, cupric nitrate, cupric trifluoromethanesulfonate, cupric chloride, cobaltous bromide, cobaltous acetate, cobaltous trifluoromethanesulfonate, ferric bromide, and ferric trifluoromethanesulfonate. Of these, cupric bromide is particularly effective and convenient. It generally gives higher yields of the ester than either the cobalt or iron compounds.

The inorganic bromide components which are used in the catalyst system of the present invention include the alkali metal bromides and hydrogen bromide. Of these, lithium bromide has been found particularly effective. When copper, cobalt or iron bromide is utilized as the copper component, this same compound can also satisfy the inorganic bromide requirement, particularly when water is also added to the reacture mixture and acetic anhydride is absent.

The inorganic nitrate components which are suitable for use in the catalyst system of the present invention include the alkali metal nitrates and nitric acid. Also included are compounds which are convertible to inorganic nitrates under the oxidative conditions of the invention process. Some of these are alkali metal nitrates, and oxides of nitrogen such as NO, $NO_2$, and the like. When cupric nitrate is used as the copper component, this compound can also serve as a nitrate component. Alkali metal nitrates such as lithium nitrate have been found particularly convenient and effective.

The conditions under which the oxidation process of the present invention is carried out are those conditions of temperature and pressure under which the reaction mixture is substantially in the liquid phase. Generally the temperature is maintained in the range of about 50° to about 200° C, more usually about 150° to about 170° C. The partial pressure of oxygen in the system will generally be in the range of about 5 to about 500 psig ($3.4 \times 10^4 - 3.4 \times 10^6$ Pa), more usually about 10 to about 100 psig ($6.9 \times 10^4 - 6.9 \times 10^5$ Pa). Air can be used as the source of oxygen, if desired, or the molecular oxygen can be diluted with nitrogen or with other inert gases. The amount of oxygen present within the reaction zone will, in any event, be at least the theoretical amount to oxidize the alkyl groups present to the extent desired and will generally be in excess of that theoretical amount. The process can be carried out either batchwise or continuously and the reaction time will depend on the specific components of the reaction mixture but will generally be in the range of about 0.1 to about 30 hours, more frequently about 0.5 to about 4 hours.

The other components of the reaction mixture will generally be present in amounts as shown in the following table. The amounts are in terms of moles (or millimoles) per mole of alkyl-substituted aromatic feedstock. Copper, cobalt, iron, bromide and nitrate compounds are calculated in terms of their ions.

| Component | Broad | Preferred |
|---|---|---|
| Carboxylic Acid | about 0.1 to about 100 mole/mole | about 1 to about 10 mole/mole |
| Acetic Anhydride | about 0 to about 100 mole/mole | about 0.2 to about 10 mole/mole |
| Water | about 0 to about 10 mole/mole | about 0 to about 2 mole/mole |
| Copper, cobalt, or iron | about 0.1 to about 100 millimole/mole | about 1 to about 50 millimole/mole |
| Bromide Compound | about 10 to about 1200 millimole/mole | about 100 to about 600 millimole/mole |
| Nitrate Compound | about 0 to about 200 millimole/mole | about 10 to about 100 millimole/mole |

Generally speaking, the addition of water to the reaction zone promotes aldehyde and acid formation. The relative absence of water, particularly when acetic anhydride is used, decreases ring bromination. The presence of nitrate improves the conversion in a given reaction time but can increase the formation of bromine-containing products at low temperatures, particularly when bromide concentration is high. Lower reaction temperatures promote the production of bromine-containing by-products.

After leaving the reaction zone, the reaction mixture can be separated by conventional methods such as by fractional distillation to isolate and recover the desired products. Incompletely oxidized products can be recycled as well as other components of the reaction mixture which have not been consumed.

In the embodiment in which alkyl-substituted organic feeds are converted to the corresponding aromatic alcohols, the first step is identical with the catalytic oxidation step described earlier. In this step, a substantial portion of a suitable aromatic feed is converted to an ester of the monocarboxylic acid which is present in the oxidation zone. The aromatic ester is separated from the reaction mixture of the catalytic oxidation step and is isolated. It is then subjected to a hydrolysis step wherein the aromatic alcohol is liberated and the monocarboxylic acid is regenerated for recycle to the oxidation step.

Any suitable conditions for hydrolysis for the ester can be used. Hydrolysis is readily carried out using excess water and at elevated temperatures, for example 50°–100° C. The hydrolysis is catalyzed by the presence of small amounts of either acids or alkalies. Trace quantities of relatively strong acids such as sulfuric, hydrochloric, trifluoroacetic acid, etc., are effective. Any reaction conditions, including conditions of temperature, time and pressure, which will substantially hydrolyze the ester can be employed.

This multi-step embodiment of the present invention is further illustrated by reference to the FIGURE which is a schematic diagram of the process. In the FIGURE, aromatic feed in line 1 passes into oxidation zone 3 where it contacts, under reaction conditions, catalyst components from line 5, carboxylic acid from line 7, and molecular oxygen from line 9. The reaction effluent from oxidation zone 3 passes via line 11 into separation zone 13. Unconverted aromatic feed, carboxylic acid and catalyst components are returned to oxidation zone 3 via line 15. Oxygenated products such as aldehydes, acids, etc., possibly including some aromatic alcohols, leave process via line 17. Other products, generally heavier, pass from the process via line 19.

Aromatic esters pass via line 21 into hydrolysis zone 23 where they contact hydrolysis chemicals such as catalyst and water entering via line 24. The reaction mixture from hydrolysis zone 23 is passed via line 25 into separation zone 27 from which aromatic alcohol product is removed via line 29. Liberated carboxylic acid is recycled to oxidation zone 3 via line 31 and line 7. Unconverted aromatic ester and recycle hydrolysis chemicals return to hydrolysis zone 23 via line 35. Make-up hydrolysis chemicals, as required, pass into line 35 via line 39. Similarly, make-up carboxylic acid passes into line 31 via line 33 and make-up catalyst components pass into line 15 via line 37.

Separation zones 13 and 27 comprise one or more conventional separation units which can contain fractionating columns, absorption towers, adsorption beds, filters, etc., as required to carry out the indicated separation. Separation by fractional distillation is generally convenient. Oxidation zone 3 and hydrolysis zone 23 can comprise one or more conventional reactors operating either in parallel or in sequence. The oxidation reaction and the hydrolysis reaction can be carried out either batchwise or continuously.

The products which are obtainable by use of the present invention process are those corresponding to the feedstock wherein the alkyl substituents have been at least partially oxidized to form groups such as alcohol, ketone, aldehyde, acid, or ester groups. The process is particularly effective for producing compounds having alcohol or aldehyde groups. Under the conditions of the reaction the alcohol products are largely in the form of esters which correspond to the specific carboxylic acid present in the reaction zone. When more than one alkyl substituent is present on the feedstock molecule, some or all of these can be oxidized, at least partially, depending upon the severity of the reaction conditions.

The oxygen-containing aromatic products of the present invention have a wide utility. For example, benzoic acid and benzyl alcohol are articles of commerce, being used in various agricultural, pharmaceutical and chemical intermediate applications.

The invention can be further illustrated by the following examples. In each of the examples, batch runs were carried out in a 500 ml glass-lined rocking autoclave. After charging the reactor with the indicated liquid and solid components, the reactor was pressured, except as noted, with 50 psig (at 24° C) initial oxygen pressure.

EXAMPLE I

A series of runs was carried out to illustrate the oxidation of toluene. Batch reactions of mixtures having the indicated compositions were subjected to the indicated reaction conditions. After the reaction period, the reaction mixtures were subjected to separation and analysis procedures which included dilution with water, extraction with pentane, and analysis of the pentane extract using gas-liquid chromatography, the analyses being reported in area percent. The conversion of the feedstock and the selectivity to specific products was computed from these analyses. The conditions and results of these runs are shown in Table I on the following page.

increase of bromine-containing by-products. Runs 6, 5, and 7 carried out with increasing amounts of nitrate components illustrate the effect of increasing the conversion. Runs 8 and 9 illustrate that sodium bromide can replace lithium bromide, though with less effectiveness, and that the presence of a nitrate component also increases the conversion of this system. Comparing invention run 10 with control run 11 clearly shows that the catalyst system requires a component such as cupric bromide to provide high conversion and high selectivity to oxygenated products. Comparison of invention run 10 with control run 12 clearly illustrates that a bromide component must be present for satisfactory conversion and selectivity to oxygenated products.

Invention run 13 shows that acetic anhydride can be absent and added water can be present in the invention process. It also shows that the copper bromide component can be the source of both the copper component and the bromide component. However, runs 14 and 15 show that this is not desirable unless some water is added to the system as in run 13. In the absence of added water, run 14 showed no conversion after three hours but a similar system showed significant conversion utilizing a four hour run and a greater quantity of lithium nitrate. Invention run 16 shows that cupric nitrate can be used as both the copper component and the nitrate component. Invention run 17 shows that copper acetate is an alternative to copper bromide.

EXAMPLE II

TABLE I

| | Oxidation of Toluene | | | | | | | | | | | | | | | | |
|---|---|---|---|---|---|---|---|---|---|---|---|---|---|---|---|---|---|
| Run No. | 1 | 2 | 3 | 4 | 5 | 6 | 7 | 8 | 9 | 10 | 11 | 12 | 13 | 14 | 15 | 16 | 17 |
| Temp., °C | 100 | 125 | 150 | 170 | 150 | 150 | 150 | 150 | 150 | 150 | 150 | 150 | 150 | 150 | 150 | 150 | 150 |
| Time, hrs. | 4 | 2 | 1 | 1 | 1 | 1 | 1 | 4 | 3 | 1 | 1 | 22.4 | 4 | 3 | 4 | 3 | 4 |
| Charge | | | | | | | | | | | | | | | | | |
| Tol., moles | 0.19 | 0.19 | 0.19 | 0.19 | 0.19 | 0.19 | 0.19 | 0.19 | 0.19 | 0.19 | 0.19 | 0.19 | 0.19 | 0.19 | 0.19 | 0.19 | 0.19 |
| HOAc, ml | 50 | 50 | 50 | 50 | 50 | 50 | 50 | 50 | 50 | 50 | 50 | 50 | 50 | 50 | 50 | 50 | 50 |
| $Ac_2O$, ml | 5 | 5 | 5 | 5 | 0 | 0 | 0 | 10 | 10 | 10 | 10 | 10 | 0 | 0 | 0 | 0 | 0 |
| $H_2O$, ml | 0 | 0 | 0 | 0 | 0 | 0 | 0 | 0 | 0 | 0 | 0 | 0 | 5 | 0 | 0 | 0 | 0 |
| $CuBr_2$, g | 1 | 1 | 1 | 1 | 1 | 1 | 1 | 1 | 1 | 1 | 0 | $1.6^b$ | 1 | 1 | 1 | $1^c$ | $1^d$ |
| LiBr, g | 5 | 5 | 5 | 5 | 5 | 5 | 5 | $5^a$ | $5^a$ | 5 | 5 | 0 | 0 | 0 | 0 | 5 | 5 |
| $LiNO_3$, g | 0.2 | 0.2 | 0.2 | 0.2 | 0.2 | 0.05 | 1 | 0 | 0.2 | 0.05 | 0.2 | 0.2 | 0.2 | 0.05 | 1 | 0 | 0 |
| Conv. % | 41 | 60 | 59 | 49 | 60 | 54 | 68 | 9 | 30 | 48 | 28 | 5 | 36 | 0 | 13 | 63 | 46 |
| Select., $\%^e$ | | | | | | | | | | | | | | | | | |
| Acetate | 12.2 | 46.0 | 84.2 | 70.2 | 70.5 | 66.7 | 64.7 | 76.1 | 74.7 | 60.8 | 48.3 | 23.4 | 44.0 | | 35.6 | 74.4 | 72.7 |
| Aldehyde | 3.7 | 8.1 | 6.6 | 3.1 | 10.3 | 13.6 | 10.9 | 23.9 | 16.2 | 14.8 | 5.0 | 14.9 | 41.2 | | 23.5 | 9.4 | 17.1 |
| Acid | | 1.0 | 2.0 | | 1.5 | 2.4 | 3.4 | | 6.1 | 3.3 | 3.8 | | 5.9 | | | 2.2 | 4.5 |
| Bromo | 42.3 | 17.4 | 4.9 | 18.0 | 10.7 | 9.0 | 12.7 | | 2.9 | 3.1 | 24.1 | | 2.5 | | 6.1 | 8.5 | 1.1 |
| Bromide | 40.1 | 25.3 | | 2.2 | 2.3 | 3.9 | 0.7 | | | 14.8 | 15.2 | | 0.4 | | 8.3 | 0.9 | 1.3 |
| Other | 1.8 | 2.2 | 2.4 | 6.4 | 5.0 | 4.4 | 7.5 | | | 3.3 | 3.6 | 61.7 | 5.9 | | 26.5 | 4.7 | 3.2 |

Notes:
$^a$NaBr instead of LiBr
$^b$Cu(CF$_3$SO$_3$)$_2$ instead of CuBr$_2$
$^c$Cu(NO$_3$)$_2$ . 3H$_2$O instead of CuBr$_2$
$^d$CuAc$_2$ . H$_2$O
$^e$Oxygenated products of toluene are benzyl acetate, benzaldehyde, benzoic acid, bromotoluenes, benzyl bromide, respectively.

In Table 1, invention runs 1–4 illustrate operability over a range of temperatures. With this specific system, it is seen that maximum conversions and selectivity to oxygenated products are obtained at about 150° C. Comparison of run 3 with run 5 shows that the acetic anhydride is optional but that its absence causes the Another series of runs was carried out in which p-tert-butyltoluene (PTBT) was oxidized to oxygenated products. These runs were carried out in essentially the same manner of those in Example I. The essential conditions and results of these runs are shown in Table II on the following page.

TABLE II

| | Oxidation of p-tert-Butyltoluene (PTBT) | | | | | | | | | |
|---|---|---|---|---|---|---|---|---|---|---|
| Run No. | 1 | 2 | 3 | 4 | 5 | 6 | 7 | 8 | 9 | 10 |
| Temp., °C | 150 | 150 | 150 | 150 | 150 | 150 | 150 | 150 | 150 | 150 |
| Time, hrs. | 2 | 1.6 | 1 | 2 | 3 | 2 | 2 | 4 | 4 | 1.5 |
| Charge | | | | | | | | | | |
| PTBT, moles | 0.11 | 0.11 | 0.11 | 0.11 | 0.11 | 0.11 | 0.11 | 0.11 | 0.11 | 0.19 |
| HOAc, ml | 50 | 50 | 50 | 50 | 50 | 50 | 50 | 50 | 50 | 50 |
| $Ac_2O$, ml | 5 | 5 | 5 | 10 | 0 | 10 | 0 | 10 | 10 | 0 |
| $H_2O$, ml | 0 | 0 | 0 | 0 | 0 | 0 | 5 | 0 | 0 | 5 |
| $CuBr_2$, g | 1 | 1 | 1 | 1 | 1 | 1 | 1 | $1.6^a$ | $1.6^a$ | 1 |

TABLE II-continued

| | Oxidation of p-tert-Butyltoluene (PTBT) | | | | | | | | | |
|---|---|---|---|---|---|---|---|---|---|---|
| Run No. | 1 | 2 | 3 | 4 | 5 | 6 | 7 | 8 | 9 | 10 |
| LiBr, g | 5 | 5 | 5 | 5 | 5 | 5 | 5 | 5 | 0 | 0 |
| LiNO$_3$, g | 0 | 0.01 | 0.05 | 0 | 0 | 0 | 0 | 0 | 0 | 0 |
| Conv., % | 51 | 61 | 80 | 57 | 63 | 57 | 58 | 55 | 0 | 35 |
| Select., %[b] | | | | | | | | | | |
| Acetate | 65.0 | 59.6 | 61.1 | 67.7 | 55.5 | 67.7 | 39.6 | 63.3 | | 27.5 |
| Aldehyde | 24.2 | 24.2 | 16.3 | 25.3 | 27.7 | 25.3 | 34.2 | 23.2 | | 54.0 |
| Acid | 8.0 | 13.4 | 8.2 | 5.4 | 13.3 | 5.4 | 20.1 | 11.1 | | 14.2 |
| Bromo | 1.0 | 1.1 | 9.7 | | 1.6 | | 2.8 | 0.6 | | 0.8 |
| Bromide | | | | | | | | | | |
| Other | 2.0 | 1.6 | 4.8 | 1.6 | 1.9 | 1.6 | 3.3 | 1.8 | | 3.5 |

Notes:
[a]Cu(CF$_3$SO$_3$)$_2$ instead of CuBr$_2$
[b]Oxygenated products are p-tert-butylbenzyl acetate, p-tert-butylbenzaldehyde, p-tert-butylbenzoic acid, bromo-p-tert-butyltoluenes, p-tert-butylbenzyl bromide, respectively.

Invention runs 1, 2 and 3 of Table II show the effect of the presence of a nitrate in the reaction system. Increasing amounts of nitrate increase the conversion. Comparing invention runs 4 and 5 show that acetic anhydride is operable in the invention process and that its presence increases the selectivity to oxygenated products. Invention runs 6, 5 and 7 illustrate the effect of water on the distribution of products. In essentially anhydrous run 6, the acetate is strongly favored. Eliminating the acetic anhydride in run 5 and, still further, adding water as in run 7 reduces the acetate product and increases the aldehyde and acid products. Invention run 8 compared with control run 9 shows that a bromide component is essential to the invention process. Invention run 10 shows that copper bromide can act as both the copper component and the bromide component, particularly when water is added to the system.

EXAMPLE III

In a manner similar to that of preceding Examples I and II, a number of runs were carried out in which toluene or p-tert-butyltoluene (PTBT) were oxidized using cobalt-containing or iron-containing catalyst system. The essential conditions and results of these runs are shown in Table III on the following page.

vention run 4 is similar to run 1 except that the reaction temperature is lower and a longer reaction time is required.

Invention runs 5, 6 and 7 illustrate that the addition of water component to the reaction system increases the selectivity to aldehyde oxygenated product. Comparing invention run 8 with invention run 9 illustrates the benefit of including a nitrate in the reaction mixture, in that the conversion is increased.

Invention runs 10 and 11 illustrate that the p-tert-butyltoluene can also be converted with high conversion and high selectivity to oxygenated products with cobalt-containing catalyst systems. Invention runs 12 and 13 show that the p-tert-butyltoluene can also be converted in high conversion and high selectivity to oxygenated products with an iron-containing catalyst system both in the presence or absence of acetic anhydride or added water. However, at comparable conditions the copper catalysts are more selective in producing ester products than the cobalt or iron catalysts.

EXAMPLE IV

In a manner similar to that of preceding Examples, other exploratory runs were carried out on several other alkyl-substituted aromatics using the catalyst sys-

TABLE III

| | Oxidation Using Cobalt and Iron | | | | | | | | | | | | |
|---|---|---|---|---|---|---|---|---|---|---|---|---|---|
| Run No. | 1 | 2 | 3 | 4 | 5 | 6 | 7 | 8 | 9 | 10 | 11 | 12 | 13 |
| Temp., °C | 150 | 150 | 150 | 125 | 150 | 150 | 150 | 150 | 150 | 150 | 150 | 150 | 150 |
| Time, Hrs. | 1 | 1.2 | 4 | 29 | 0.25 | 4 | 18.2 | 1 | 3 | 0.75 | 3 | 3 | 3.5 |
| Charge | | | | | | | | | | | | | |
| Tol., moles | 0.19 | 0.19 | 0.19 | 0.19 | 0.19 | 0.19 | 0.19 | 0.19 | 0.19 | 0.19[c] | 0.19[c] | 0.11[c] | 0.11[c] |
| HOAc, ml | 50 | 50 | 50 | 50 | 50 | 50 | 50 | 50 | 50 | 50 | 50 | 50 | 50 |
| Ac$_2$O, ml | 10 | 10 | 10 | 10 | 0 | 0 | 0 | 10 | 10 | 10 | 0 | 10 | 0 |
| H$_2$O, ml | 0 | 0 | 0 | 0 | 1 | 5 | 20 | 0 | 0 | 0 | 5 | 0 | 5 |
| CoBr$_2$, g | 1 | 1.6[a] | 1.6[a] | 1 | 1 | 1 | 1 | 1.3[b] | 1.3[b] | 1 | 0.2 | 1.3[b] | 1.3[b] |
| LiBr, g | 0 | 5 | 0 | 0 | 0 | 0 | 0 | 5 | 5 | 0 | 0 | 5 | 0 |
| LiNO$_3$, g | 0 | 0 | 0 | 0 | 0 | 0 | 0 | 0.2 | 0 | 0 | 0 | 0 | 0 |
| Conv.,% | 44 | 40 | 0 | 41 | 28 | 39 | 31 | 56 | 31 | 43 | 29 | 46 | 42 |
| Select., % | | | | | | | | | | | | | |
| Acetate | 55.4 | 55.5 | | 59.6 | 19.1 | 33.7 | 23.6 | 64.6 | 35.4 | 57.8 | 21.1 | 32.2 | 20.1 |
| Aldehyde | 20.4 | 30.1 | | 13.1 | 56.7 | 46.0 | 57.6 | 9.7 | 50.8 | 23.5 | 35.3 | 49.6 | 50.9 |
| Acid | 16.5 | 12.4 | | 17.0 | 16.3 | 16.8 | 14.9 | 1.1 | 5.8 | 7.4 | 40.1 | 16.7 | 21.8 |
| Bromo | 0.7 | | | 0.2 | | | 2.6 | 11.2 | 1.3 | | | 0.6 | 2.1 |
| Bromide | 6.1 | 0.7 | | | 6.0 | | | 9.2 | 2.6 | 0.9 | | | |
| Other | 0.9 | 1.2 | | 9.9 | 1.8 | 3.5 | 1.3 | 3.7 | 4.0 | 0.7 | 3.5 | 0.8 | 5.0 |

Notes:
[a]Co(CF$_3$SO$_3$)$_2$ instead of CoBr$_2$
[b]FeBr$_3$·6H$_2$O instead of CoBr$_2$
[c]PTBT instead of toluene Invention run 1 of Table III shows that, somewhat unlike the corresponding copper bromide systems, the cobalt bromide can be used as both the cobalt and the bromide component under essentially anhydrous conditions to give substantial conversions and selectivity to oxygenated products. Invention run 2, when compared to control run 3, again shows that a bromide component is essential to the process of the present invention. Intem and process of the present invention. In runs utilizing 50 ml acetic acid, 10 ml acetic anhydride, 1.0 g CuBr$_2$, and 5.0 g LiBr, 0.19 mole quantities of cumene (isopropylbenzene), p-cymene, (p-isopropyltoluene) or mesitylene (1,3,5-trimethylbenzene) were oxidized with molecular oxygen to corresponding oxygenated products such as acids, aldehydes, and esters.

EXAMPLE V

The following calculated example is presented to further illustrate the two step embodiment of the invention to produce benzyl alcohol by employing both an oxidation step and a hydrolysis step.

In a combination process generally as depicted in the FIGURE, a glass-lined, stirred reactor in oxidation zone 3 is charged with 1000 moles toluene, 4700 moles acetic acid, 24 moles $CuBr_2$, 300 moles LiBr, and 15 moles $LiNO_3$. The reactor is then pressured with sufficient oxygen to provide an oxygen partial pressure of 50 psig within the reactor, then heated to 150° C and maintained at that temperature for 60 minutes.

The reactor contents are then passed into separation zone 13 containing a series of fractionating columns from which are recovered 420 moles of benzyl acetate and 180 moles of a mixture of by-products comprising benzaldehyde, benzoic acid, bromotoluenes, and benzyl bromides. About 4250 moles of acetic acid and 400 moles toluene are also recovered and returned to oxidation zone 3.

The 420 moles of benzyl acetate from separation zone 13 are conducted to a stirred stainless steel reactor in hydrolysis zone 23 and contacted with 5000 moles water and 5 moles sulfuric acid for 80 minutes at 75° C and at 25 psig.

The effluent from the hydrolysis reactor is passed into separation zone 27 containing a series of fractionators from which are recovered 410 moles of benzyl alcohol product. Also recovered are 410 moles of acetic acid which are passed back to the reactor in oxidation zone 3 where it is combined with 40 moles of make-up acetic acid and the 4250 moles acetic acid returned from separation zone 13 to make up the 4700 mole charge for the reactor in oxidation zone 3.

We claim:

1. A liquid phase process for oxygenating an alkyl-substituted aromatic compound corresponding to the generic formulas

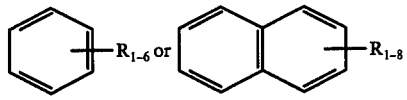

wherein each R is selected from branched or unbranched alkyl groups having from one to about 6 carbon atoms, or halogen atoms, at least one R being an alkyl group free of quaternary carbon atoms said process comprising contacting said compound with molecular $O_2$ at about 150° to about 170° C. in the presence of an alkanoic acid having from one to about 6 carbon atoms per molecule, a copper, cobalt, or iron compound soluble under the oxygenating conditions, an inorganic bromine compound and an inorganic nitrate compound.

2. A process of claim 1 wherein said carboxylic acids are present in the range of about 0.1 to about 100 moles per mole of alkyl-substituted aromatic feedstock.

3. A process of claim 1 wherein said copper, cobalt and iron compounds are selected from among cupric bromide, cuprous bromide, cupric acetate, cupric nitrate, cupric trifluoromethanesulfonate, cupric chloride, cobaltous bromide, cobaltous acetate, cobaltous trifluoromethanesulfonate, ferric bromide, and ferric trifluoromethanesulfonate.

4. A process of claim 3 wherein said copper, cobalt, and iron compounds are present in the range of about 0.1 to about 100 millimoles per mole of alkyl-substituted aromatic feedstock.

5. A process of claim 1 wherein said bromine compound is selected from among alkali metal bromides and hydrogen bromide.

6. A process of claim 5 wherein said bromide compounds are present in the range of about 10 to about 1200 millimoles per mole of alkyl-substituted aromatic feedstock.

7. A process of claim 1 wherein said contacting of an alkyl-substituted aromatic compound with molecular $O_2$ is in the presence of inorganic nitrate components selected from among alkali metal nitrates and compounds convertible to inorganic nitrates under the oxidative conditions of the process.

8. A process of claim 7 wherein the concentration of nitrate compound contacted with the alkyl-substituted aromatic compound is in the range of from about 10 to about 100 millimoles per mole of alkyl-substituted aromatic feedstock.

9. A process of claim 1 wherein said contacting of an alkyl-substituted aromatic compound with molecular $O_2$ is in the presence of acetic anhydride or water.

10. A process of claim 1 wherein the partial pressure of oxygen in the system is within the range of about 5 to about 500 psig.

11. A liquid phase process for oxygenating an alkyl-substituted aromatic compound corresponding to the generic formulas

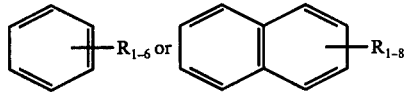

wherein each R is selected from branched or unbranched alkyl groups having from one to about 6 carbon atoms, or halogen atoms, at least one R being an alkyl group free of quaternary carbon atoms said process comprising distinct steps of:

(a) contacting said alkyl-substituted aromatic compounds with molecular $O_2$ at about 150° to about 170° C. in the presence of an alkanoic acid having from one to about 6 carbon atoms per molecule, a copper, cobalt, or iron compound soluble under the oxygenating conditions, an inorganic nitrate and an inorganic bromine compound to produce an ester of an aromatic alcohol and said carboxylic acid;

(b) separating said ester from the reaction mixture; and (c) hydrolyzing said ester to produce an aromatic alcohol and to regenerate the carboxylic acid.

* * * * *